(12) United States Patent
Bilan

(10) Patent No.: US 8,474,571 B1
(45) Date of Patent: Jul. 2, 2013

(54) LIMITED MOVEMENT EAR PIECE FOR STETHOSCOPES AND OTHER HEADPIECES

(75) Inventor: Frank Albert Bilan, Newman, CA (US)

(73) Assignee: Stethoscope Technologies, Inc., San Jose, CA (US)

( * ) Notice: Subject to any disclaimer, the term of this patent is extended or adjusted under 35 U.S.C. 154(b) by 0 days.

(21) Appl. No.: 13/352,951

(22) Filed: Jan. 18, 2012

(51) Int. Cl.
*A61B 7/02* (2006.01)

(52) U.S. Cl.
USPC ............................ 181/131; 181/135; 181/129

(58) Field of Classification Search
USPC ......................................... 181/129, 131, 135
See application file for complete search history.

(56) References Cited

U.S. PATENT DOCUMENTS

| | | | | |
|---|---|---|---|---|
| 2,803,308 | A * | 8/1957 | Di Mattia | 181/135 |
| 3,710,888 | A | 1/1973 | Peart | 181/24 |
| 4,443,668 | A * | 4/1984 | Warren | 455/351 |
| 5,002,151 | A | 3/1991 | Oliveira et al. | 181/130 |
| 6,514,213 | B1 | 2/2003 | Moteki | 600/528 |
| 7,424,123 | B2 * | 9/2008 | Shennib et al. | 381/328 |
| 7,522,743 | B2 * | 4/2009 | Dobras et al. | 381/381 |
| 7,931,027 | B2 * | 4/2011 | Topholm et al. | 128/864 |
| 8,083,022 | B2 * | 12/2011 | Gommel et al. | 181/135 |
| 2002/0085728 | A1 * | 7/2002 | Shennib et al. | 381/328 |
| 2004/0228494 | A1 * | 11/2004 | Smith | 381/67 |
| 2007/0142697 | A1 * | 6/2007 | Schneider | 600/25 |
| 2009/0321196 | A1 | 12/2009 | Bilan | 188/166 |
| 2010/0174380 | A1 * | 7/2010 | Lewis | 623/22.11 |
| 2011/0194716 | A1 * | 8/2011 | Gommel et al. | 381/328 |

* cited by examiner

*Primary Examiner* — Forrest M Phillips
(74) *Attorney, Agent, or Firm* — Girard & Equitz LLP

(57) ABSTRACT

An ear piece assembly (10, 100, 200, 300, 500, 600, 700, 800, 900, 1000) designed for a stethoscope or other headpiece, and configured to allow rotation of an ear tip (20, 120, 220, 320, 420, 520, 620) of the assembly about a central axis (relative to the rest of the assembly) and to allow limited off axis movement of the ear tip (relative to the rest of the assembly). In typical embodiments, the ear piece assembly is designed to fit a user's ear canal and stay in place during typical use without rotational or off axis movement of the ear tip relative to the ear canal, and to provide substantially more comfort to the user than would a headpiece with a conventional ear tip assembly, particularly for prolonged wearing by the user. Other aspects of the invention are a headpiece (e.g., a stethoscope headpiece) or stethoscope including an embodiment of the earpiece assembly, an ear piece housing body configured for use in an embodiment of the earpiece assembly, and an ear tip configured for use in an embodiment of the earpiece assembly.

43 Claims, 14 Drawing Sheets

LIMITED MOVEMENT EAR PIECE FOR STETHOSCOPES AND OTHER HEADPIECES

BACKGROUND OF THE INVENTION

1. Field of the Invention

The present invention relates to an earpiece assembly of a headpiece, and to stethoscopes and other headpieces that include such an earpiece assembly. In a class of embodiments, the inventive earpiece assembly includes an ear tip portion (which directly interfaces with the user's ear canal) configured to be rotatable on axis (about the earpiece assembly's longitudinal axis) relative to the rest of the earpiece assembly and to have limited freedom to pivot off axis (about at least one axis that is perpendicular to the longitudinal axis) relative to the rest of the earpiece assembly.

2. Background of the Invention

Throughout this disclosure, including in the claims, the expressions "headset," "headpiece," and "head piece" are used as synonyms to denote an apparatus configured to be worn on or positioned against a user's head. Examples of headsets are the head pieces of stethoscopes (both acoustic (or passive) and active (e.g., electronic) stethoscopes), audio headphones (of the type that include a small loudspeaker for each ear, to make audible the output of a home or portable audio system), and telephone headsets (of the type including a microphone as well as a small loudspeaker for each ear or a single one placed in the lumen structure etc. as mentioned previously).

Throughout this disclosure, including in the claims, the expression "ear piece assembly" (or "earpiece assembly" or "earpiece") denotes a subassembly (or portion) of a head piece, intended and configured to be positioned in, or otherwise in direct contact with, an ear of the head piece's user. The expression "ear tip" (or "ear tip" portion) herein denotes an element or portion of an ear piece assembly that is intended and configured to be positioned in, or otherwise in direct contact with, an ear of the ear piece assembly's user, and assumes that the ear piece assembly includes at least one other element (or portion) that is not an ear tip. Examples of ear tips include the small loudspeakers (sometimes referred to as sound transducers) of a pair of audio headphones, and the soft ear tips (which generally do not contain transducers) of the head pieces of passive stethoscopes.

Throughout this disclosure, including in the claims, the term "proximal" (with reference to a headpiece) denotes "toward" the center of the head of a user who wears the headpiece, and the term "distal" (with reference to a headpiece) denotes "away from" the center of the head of a user who wears the headpiece. Thus, a "proximal" portion (e.g., "proximal" end) of an earpiece assembly (or a subassembly of an earpiece assembly) denotes a portion of the assembly (or subassembly) located "toward" or relatively near to the center of the head of a user who wears a head piece including the assembly, and a "distal" portion (e.g., "distal" end) of an earpiece assembly (or a subassembly of an earpiece assembly) denotes a portion of the assembly (or subassembly) located "away from" or relatively far from to the center of the head of a user who wears a head piece including the assembly. An ear tip portion of an earpiece assembly is located at the proximal end of the assembly during use.

Throughout this disclosure including in the claims, the expression "active" stethoscope (or "active" sound detection device) denotes a stethoscope (or sound detection device) that includes an acoustic transducer useful for converting acoustic waves (e.g., body sounds of interest) into another form of energy.

Herein, the expression "electronic" stethoscope (or "electronic" sound detection device) denotes a stethoscope (or sound detection device) that includes an acoustic transducer useful for converting acoustic waves of interest (e.g., body sounds) into at least one electric signal. Also herein, the expression "passive" stethoscope (or "passive" sound detection device) denotes a stethoscope (or sound detection device) that does not include an acoustic transducer.

Throughout this disclosure, including in the claims, each of the expressions "acoustic transducer" and "sound transducer" denotes a device for converting acoustic waves into another form of energy. For example, one type of acoustic transducer is a typical microphone configured to convert acoustic waves into an electrical signal. Another example of an acoustic transducer is a device configured to convert acoustic waves into electromagnetic waves (e.g., visible radiation or electromagnetic radiation whose wavelength or wavelengths is or are outside the visible range), and optionally also to convert the electromagnetic waves into an electrical signal. Acoustic transducers are sometimes referred to as sound pick-ups, and are sometime referred to herein simply as transducers.

Throughout this disclosure including in the claims, the expression "axis" of an earpiece assembly (or ear tip), unless otherwise defined, generally assumes that the earpiece assembly (or ear tip) has a longitudinal axis and denotes the longitudinal axis of the earpiece assembly (or ear tip). For example, the axis of an earpiece assembly having generally cylindrical form is the assembly's central longitudinal axis.

Throughout this disclosure including in the claims, the expression "bearing" is used in a broad sense to denote a first element (e.g., unit 28 of FIG. 9, unit 128 of FIG. 13, or element 529 of FIG. 21) configured to support a second element (e.g., an ear tip) fitted onto the first element, such that the second element has freedom to rotate ("on axis," where "axis" here denotes the first element's longitudinal axis) relative to the first element. Optionally also, the second element has freedom to pivot ("off axis") relative to the first element. For example, one type of bearing is a ball joint unit (e.g., unit 28 of FIG. 9 or 10, or unit 128 of FIG. 13) having a ball portion, and configured to support an ear tip fitted onto the ball portion, such that the ear tip has freedom to rotate ("on axis") and freedom to pivot ("off axis") relative to the ball portion. Another exemplary type of bearing is an element (e.g., element 529 of FIG. 21) having a rotationally symmetric support portion (e.g., the partial conical end portion of element 529), said element being configured to support an ear tip that has been fitted onto it, such that the ear tip has freedom to rotate ("on axis") relative to the support portion.

Throughout this disclosure including in the claims, the herein used expressions "sound tube" or "tube", unless otherwise defined, generally refers a formed tube or tubes that are an integral part of the head piece portion of a complete stethoscope or other head piece assembly.

Stethoscopes are used by health care givers (primarily physicians, so that health care givers will be referred as such herein) to aid in the detection of body sounds for the purpose of diagnosing various symptoms such as heart beat anomalies or lung infections, etc. This procedure is commonly called auscultation.

In a class of embodiments, the invention pertains to a stethoscope earpiece designed to be inserted into a user's outer ear canal for purposes of efficiently transmitting sound from a remote stethoscope chest piece placed on a patient's body to the user's ear. The sound transmission is usually accomplished by one of two methods. The first and most common method is to utilize tube structures called lumens to connect the chest piece to the two ear pieces. Stethoscopes implementing this method are commonly called "acoustic" stethoscopes. The second method is to use an electronic chest piece with various sound sensing devices such as microphones. The sound sensing devices in the chest piece work with an electronic amplifier which then drives miniature loudspeakers that are generally placed in the earpiece assembly. Wires are used in the lumen to connect the speakers to the amplifier in the chest piece. A miniature loudspeaker may also be placed in the lumen structure or chest piece itself. This is well known in the art. Stethoscopes implementing this method are commonly called "electronic" or "active" stethoscopes.

Myriad devices are known in the art which attempt to improve the comfort and seal efficiency of stethoscope headpiece ear tips. Much of the art attempts to address the issues of ear tip softness, comfort of fit, ease of cleaning, etc.

The outer ear is the most external portion of the ear. The outer ear includes the pinna (the flesh covered cartilage), the ear canal, and the most superficial layer of the ear drum (also called the tympanic membrane). Portions of the ear after the ear drum such as the middle ear etc. are blocked from access to the outside world. The axis of the ear canal does not converge to the lower center of the head on the same plane as the ear canal, but rather converges slightly upwards and forward towards the upper bridge of the nose. This forward bend is roughly 10 to 15 degrees from the head's sideways horizontal axis (the Y axis in FIG. 3).

This is the reason why all good quality stethoscopes have the ear tips bent at approximately 10 degrees off the center line of the head piece. When placing the stethoscope headpiece on his ears, the physician instinctively knows to point the ear piece portions forward toward his face, i.e. the 10 degree angle is toward the back of his head. This orientation is clearly shown in FIG. 3.

The stethoscope ear tip generally fits into the distal portion of the ear canal, some 20 to 26 mm in length, whose proximal portion faces the ear drum. Depending on ear canal entry variations, the ear tip may penetrate 7 to 10 mm while deforming itself and the canal entry. Thus a seal is formed.

Once so positioned (with a seal), the ear tip is not in the position to rotate freely because of deformation and being out-of-center with reference to the imaginary ear canal rotation axes and the axis of the stethoscope headpiece arms. This will be explained in more detail in the body of this teaching.

Several devices which include rotatably mounted ear tips are described in the following references:

U.S. Pat. No. 6,514,213, to Moteki et al., describes a ball bearing in an earpiece assembly for ease of rotation. However it does not address the off axis angular changes due to the ear canal being set at an angle;

U.S. Pat. No. 5,002,151, to Oliveira et al., describes a ball and socket assembly, but in a fixed application designed for stationary hearing aids;

U.S. Pat. No. 3,710,888, to Peart, describes a rotatable sleeve assembly, allowing rotation of the ear tip in one axis, but not allowing off axis angular movement. This patent also describes an ear piece assembly including a rotatable ball, allowing rotation of the ear tip only on axis. No significant off axis angular movement is possible due to the assembly's design; and U.S. Pat. No. 2,803,308, to Di Mattia, describes a rotatable sleeve assembly, allowing rotation of the ear tip in one axis. No off axis angular movement is possible.

U.S. Pat. No. 5,002,151 (Oliveira) describes (with reference to that patent's FIG. 4a) a hearing aid ear piece including the above-mentioned ball and socket assembly. However, the hearing aid is a stationary hearing aid and the ear piece is designed to remain fixed during use. The ball and socket assembly is designed to allow the ear tip to be easily attached and detached from the rest of the hearing aid, and is said to be a substitute for a bayonet attachment assembly. Oliveira thus teaches interchangeable use of a bayonet or ball and socket assembly for fixedly (but removably) attaching an ear tip to a hearing aid.

FIG. 4 is a cross section drawing of an earpiece described in the Moteki patent (U.S. Pat. No. 6,514,213) in which the inner race 6b of a ball bearing 5a is mounted on earpiece tube 8a, while the outer race 6c is fastened to a hub 6a which in turn is fastened to the ear tip 7a. This allows the ear tip to have free rotation about the ear piece axis as hub 6a rolls on balls 9a of bearing 5a. No provision is made for earpiece off axis movement.

FIG. 5 is a cross section drawing is shown of an earpiece described in the Peart patent (U.S. Pat. No. 3,710,888). This earpiece assembly uses a sleeve 5b screwed onto earpiece tube 8b. A second sleeve 6d is slipped over and swaged over distal end (the left end, in FIG. 5) of sleeve 5b. The swaging is loose, allowing "on axis" rotation of sleeve 6d over sleeve 5b (relative to the center axis of tube 8b). Sleeve 6d is fastened to ear tip 7b. This allows the ear tip 7b and sleeve 6d to rotate about the center axis of earpiece tube 8b. No provision is made for off axis movement of ear tip 7b or sleeve 6d.

FIG. 6 is a cross section drawing of another earpiece described in the Peart patent. This earpiece assembly uses a ball 5c bonded onto earpiece tube 8c. Ear tip 7c is placed over the ball 5c, with freedom to rotate relative to ball 5c and tube 8c about the earpiece's longitudinal axis. Although the design allows "on axis" rotation of ear tip 7c (around the center longitudinal axis of tube 8c), the close fit of ear tip 7c's distal portion 9c around tube 8c would prevent significant off axis pivoting of ear tip 7c relative to tube 8c.

Prevention of off axis pivoting of ear tip 7c was evidently a deliberate design of Peart in view of Peart's teaching at col. 1, lines 16-35, that although an ear tip could be mounted with unrestricted rotatability (about all axes) relative to the user's ear canal, restricted ear tip rotatability (rotatability only about an axis parallel to the ear canal's longitudinal axis) "suffices since it substantially eliminates, completely, tangential stress on the ear canal tissues. While this permits some stress to be exerted transverse to the axis of rotation, and along it, the usual movement of the stethoscope is not in such directions as would produce these types of stress, and, further, the ear canals are less vulnerable thereto." The present inventor has recognized that this teaching of Peart is incorrect for a number of reasons, including the reason that, in some stethoscope users, the ear canal is very sensitive in all directions of stress and sustained pressure. The present inventor has addressed stethoscope user ear comfort issues in US Patent Application Publication No. 20090321196, published Dec. 31, 2009 (entitled Asymmetric Tension Adjustment Mechanism and Head Piece including Same), and the present invention addresses such comfort issues in a very different way to be described in detail below.

Peart notes at col. 1, lines 21-27, that ear tips can be connected to sound tubes "by ball and socket joints, so that when the eartips are in place in the ear canals, the axis of rotation between sound tubes and eartips can have any angular orientations whatsoever." However, Peart does not suggest that there should be any limitation on the range in which an ear tip should be allowed to rotate about any particular axis. In contrast, the present inventor has recognized that although, for practical use, a full range of axial ("on axis") rotation of an ear tip can be allowed over the full range (i.e., by any amount from 0 to 360 degrees about the axis of an ear piece assembly to which the ear tip is mounted), and the ear tip should be allowed significant freedom to pivot off axis as well as on axis, the ear tip's off axis deviation should typically be limited to be not be more than about ten degrees (relative to the axis of the ear piece assembly). The reason for this is that if an ear tip moves (e.g., is bent) off axis too far, it becomes cumbersome to insert into the ear canal. Additionally, it can easily fall off its socket when inadvertently rubbed up against clothing, coat pockets, or other objects.

Typical embodiments of the present invention achieve desirable (substantial, but limited) ear tip off axis rotatability, and substantial (preferably unlimited) "on axis" rotatability, by splitting up the functions of ear tip rotation and off axis movement restriction. This will be further explained in detail below.

BRIEF DESCRIPTION OF THE INVENTION

In a class of embodiments, the invention is an ear piece assembly (e.g., an ear piece for a stethoscope headpiece) configured to achieve compound axis ear tip movement in either of two ways. In some embodiments, the ear piece assembly includes an ear tip mounted as an element of a ball and socket assembly so as to have a limited range of off-axis pivoting motion (and freedom to rotate on axis). In another class of embodiments, an ear piece is designed to rotate on a shaft around the ear piece axis, while flexing slightly in the any direction orthogonal to the ear piece axis.

The ball and socket assembly's configuration lends itself to movement in any direction given the constraints of its ball mount and other external limiting devices. The ball and socket assembly is easy to insert and remove for cleaning and adjusts comfortably to various shapes and sizes of ear canal entry configurations.

The ear piece assembly including a shaft and a flexing ear tip portion also works well, but its ear tip may be more complex to mold than is the ear tip of the ear piece with ball and socket assembly.

In a class of embodiments, the inventive earpiece assembly includes an ear tip portion (which directly interfaces with the user's ear canal) configured to be rotatable on axis (about the earpiece assembly's longitudinal axis) relative to the rest of the earpiece assembly and to have limited freedom to pivot off axis (about at least one axis that is perpendicular to the longitudinal axis) relative to the rest of the earpiece assembly.

Other aspects of the invention are a headpiece (e.g., a stethoscope headpiece) or stethoscope including any embodiment of the inventive earpiece assembly, an ear piece housing body configured for use in an embodiment of the inventive earpiece assembly, and an ear tip configured for use in an embodiment of the inventive earpiece assembly.

Figure 4:
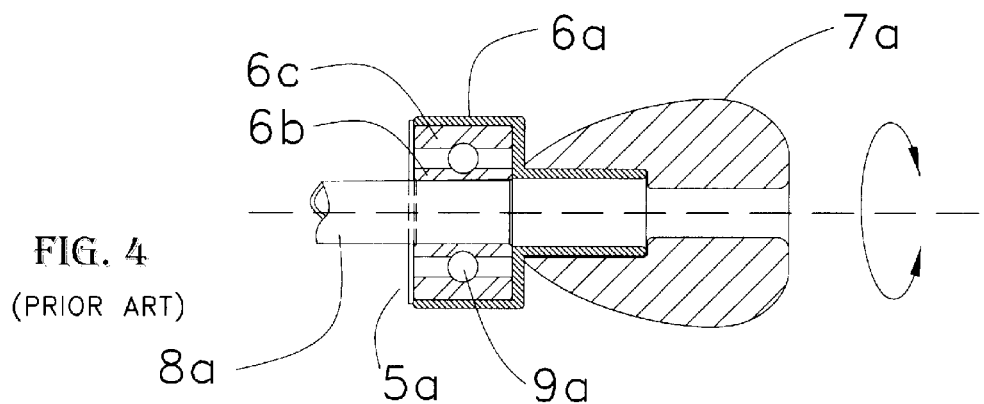
Figure 5:
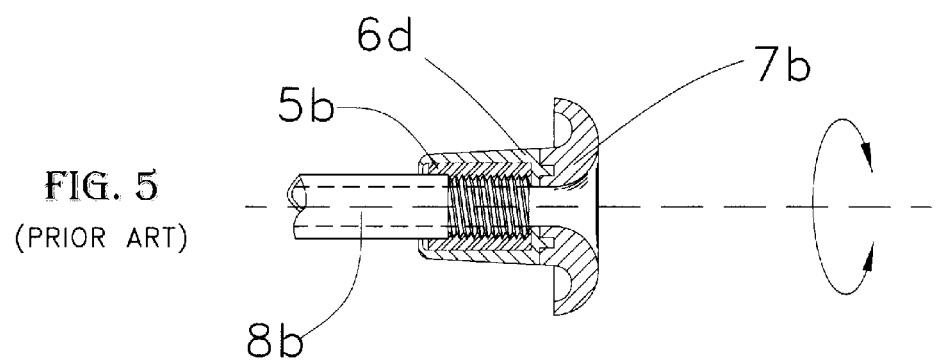
Figure 6:
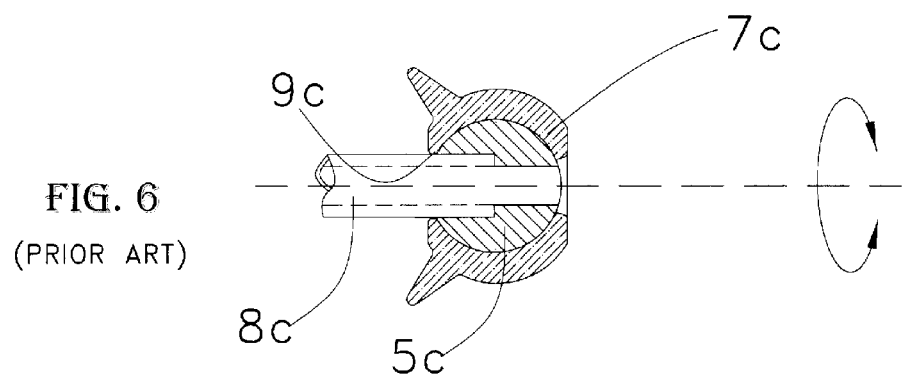

Each of FIGS. 4, 5 and 6 is a cross-sectional view of a conventional stethoscope ear piece.

Figure 7:
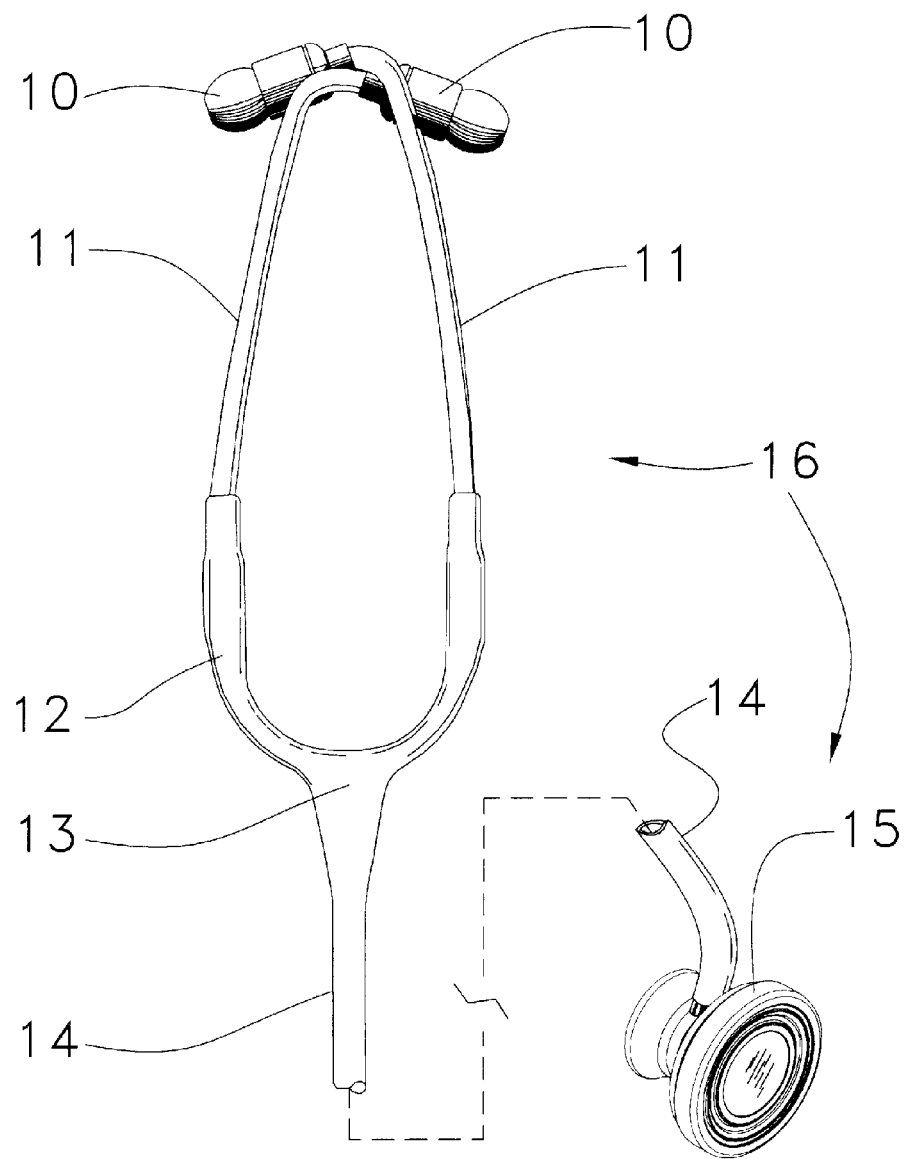

FIG. 7 is a partial, elevational view of a stethoscope which includes a pair of ear pieces (10). Each of ear pieces 10 is designed in accordance with a first embodiment of the invention.

Figure 8:
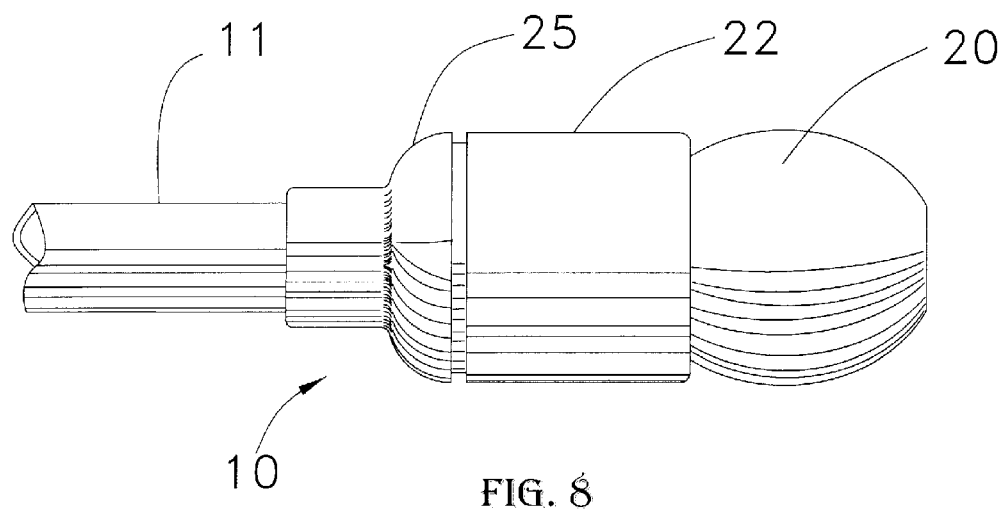

FIG. 8 is a side elevational view of ear piece 10 (of FIG. 7) showing the basic external structure of the first embodiment of the invention.

Figure 9:
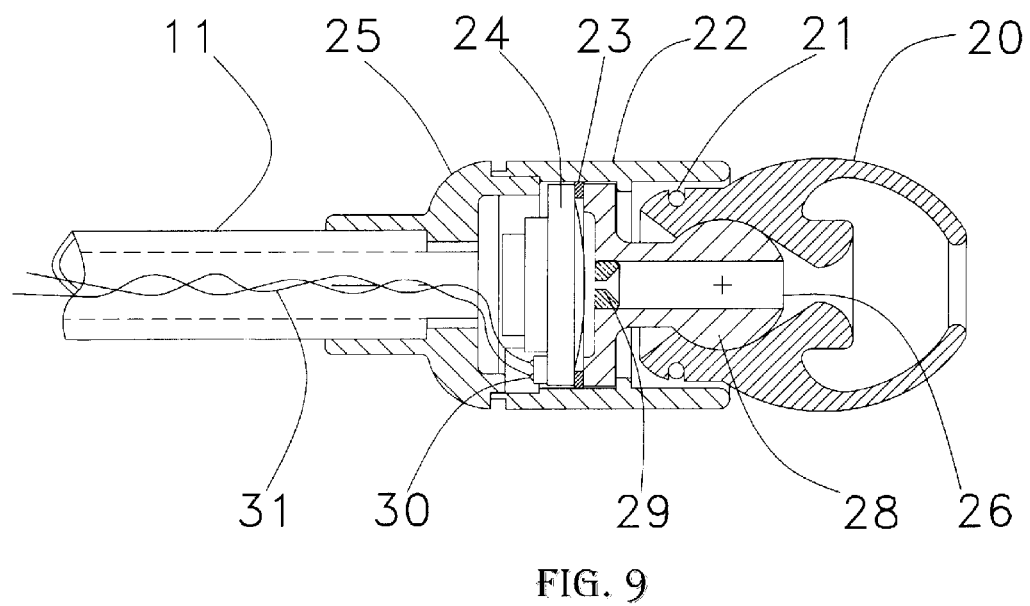

FIG. 9 is a cross-sectional view, showing the basic internal structure of the first embodiment of the invention.

Figure 10:
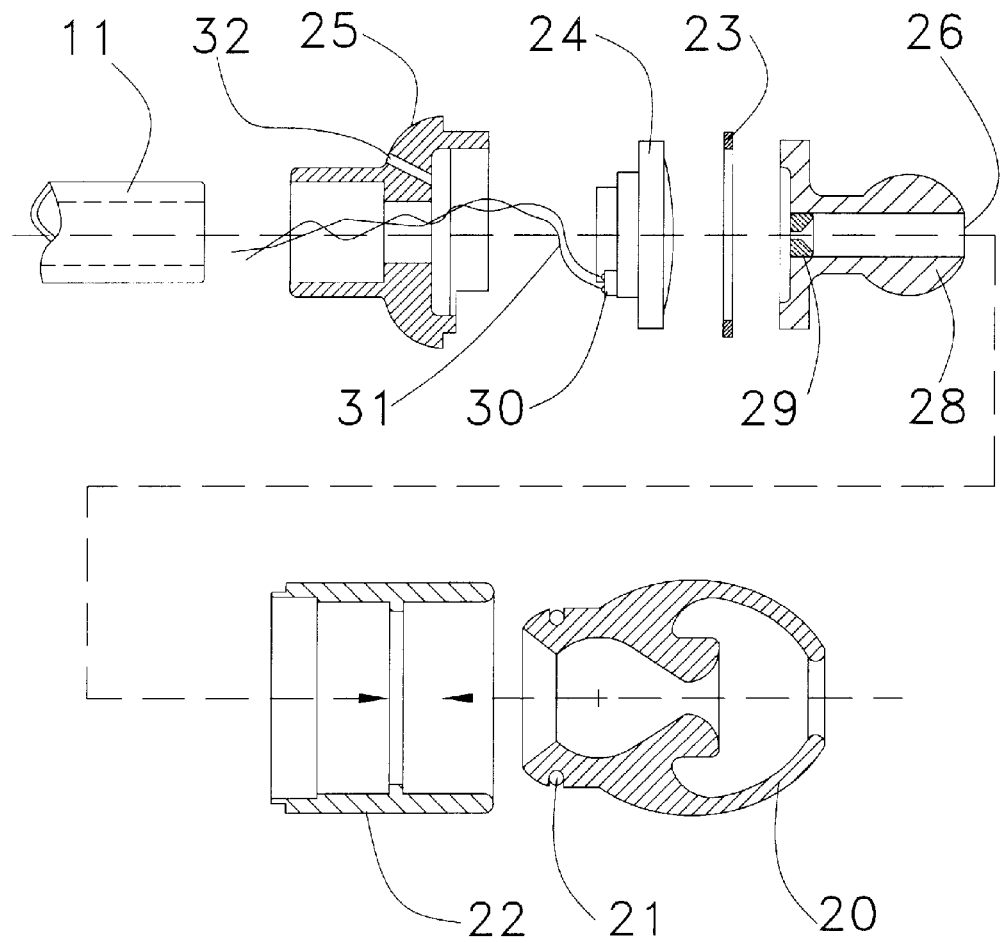

FIG. 10 is an exploded view of the first embodiment of the present invention.

Figure 11:
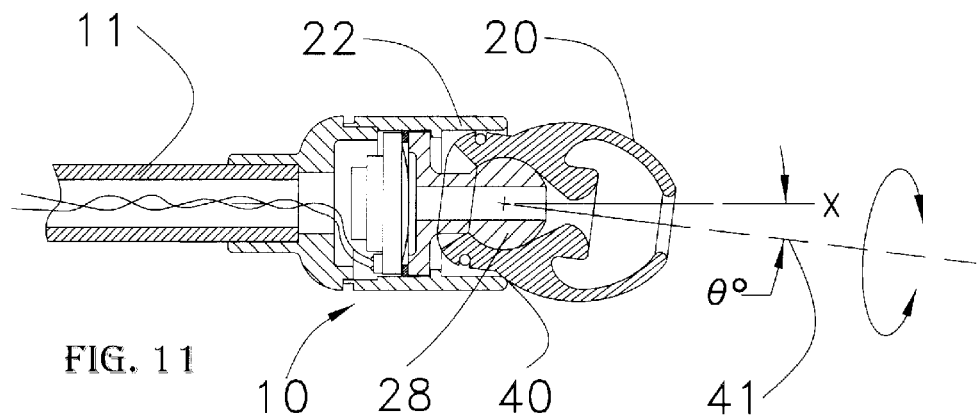

FIG. 11 is a cross sectional view of an ear piece of the first embodiment of the inventive ear tip swiveling in a downward direction.

Figure 12:
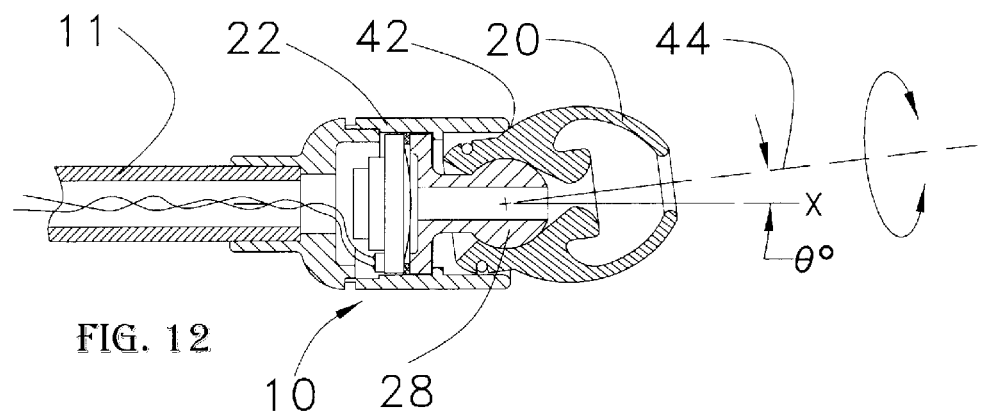

FIG. 12 is a cross sectional view of an ear piece of the first embodiment of the inventive ear tip swiveling in an upward direction.

Figure 13:
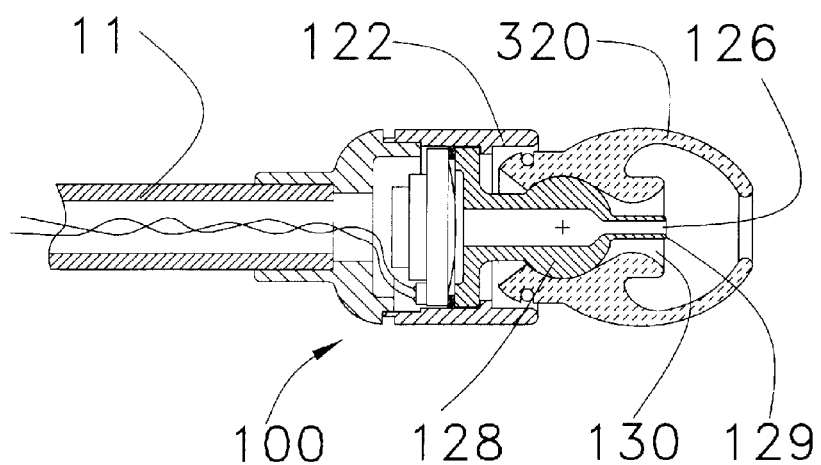

FIG. 13 shows the basic internal structure of a second embodiment of the present invention.

Figure 14:
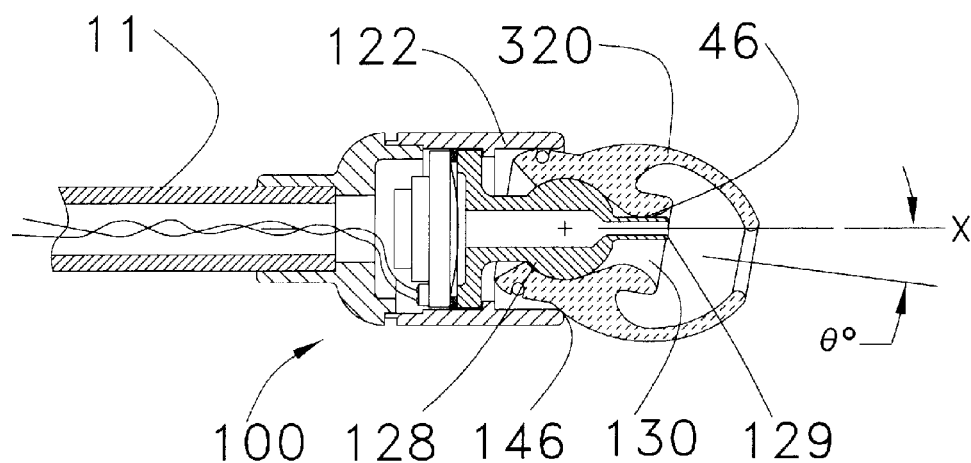

FIG. 14 is a cross sectional view of the second embodiment of the inventive ear tip, with the ear tip swiveling in a downward direction.

Figure 15:
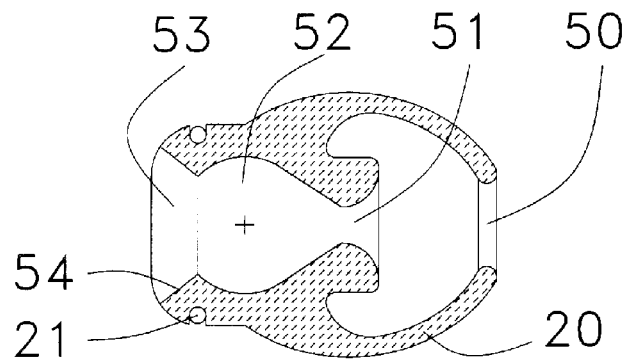
Figure 16:
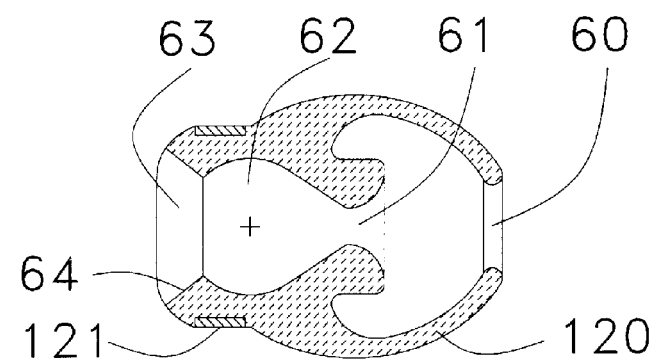
Figure 17:
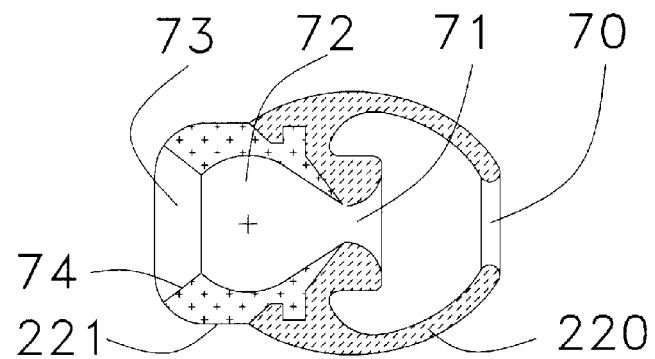

FIGS. 15, 16 and 17 show various structures and compositions of embodiments of the ear tip section of the inventive ear piece.

Figure 18:
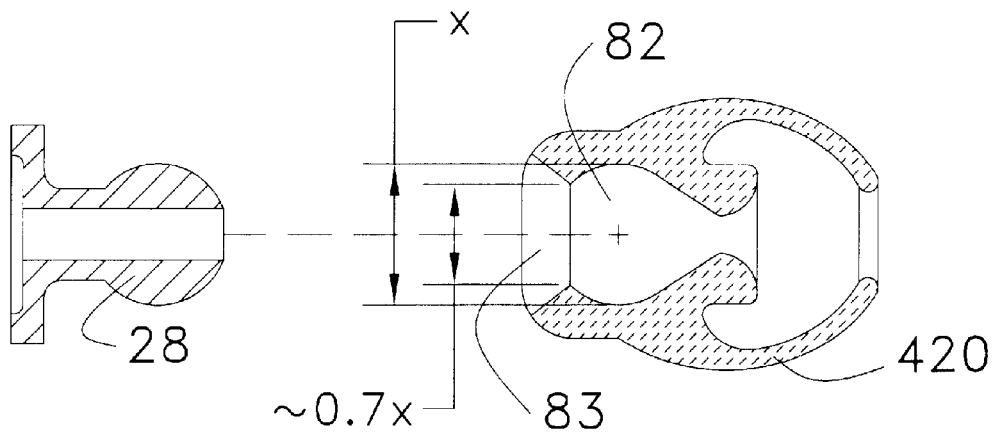
Figure 19:
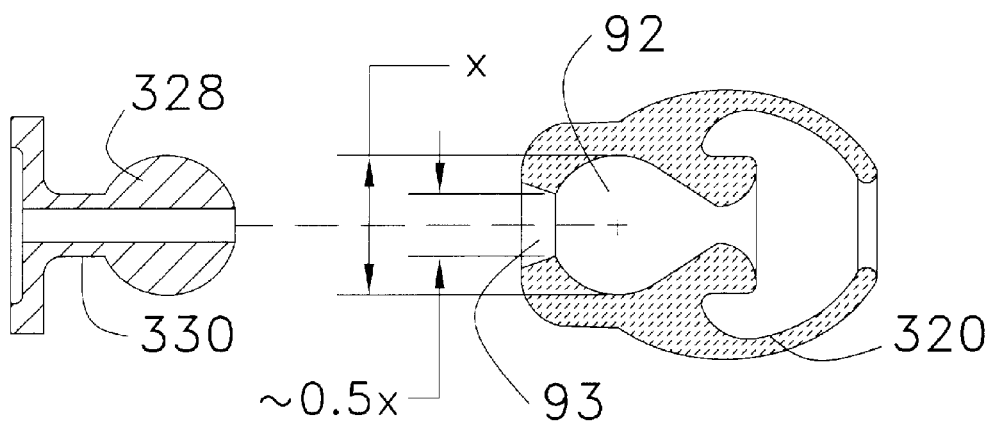
Figure 20:
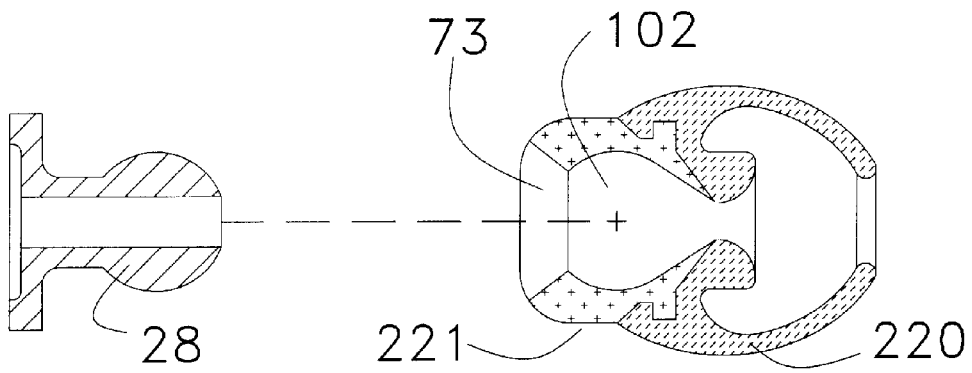

FIGS. 18, 19 and 20 show various dimensional variations and compositions of embodiments of the ear tip section of the inventive ear piece.

Figure 21:
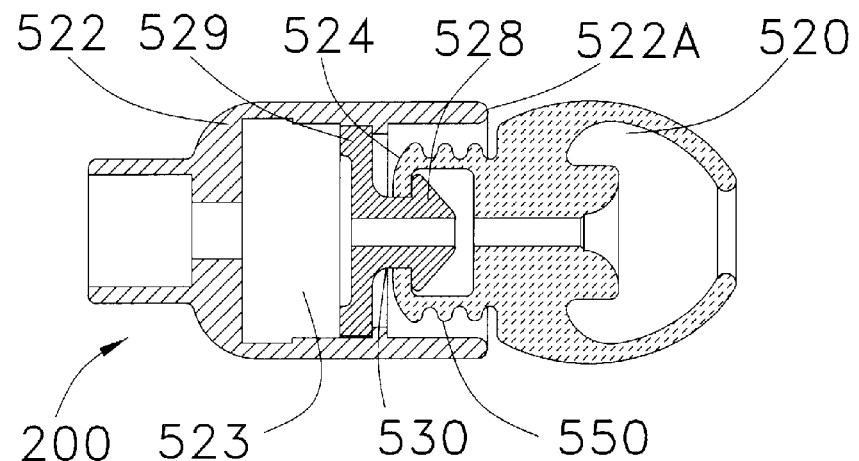

FIG. 21 is a cross section of the basic internal structure of a third embodiment of the present invention.

Figure 22:
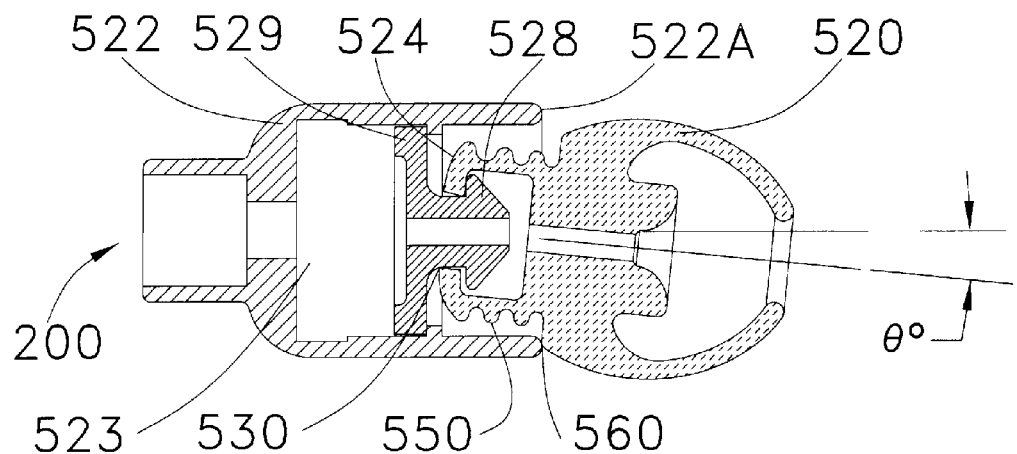

FIG. 22 is a cross section of the basic internal structure of the third embodiment of the invention with its ear tip portion flexing downward.

Figure 23:
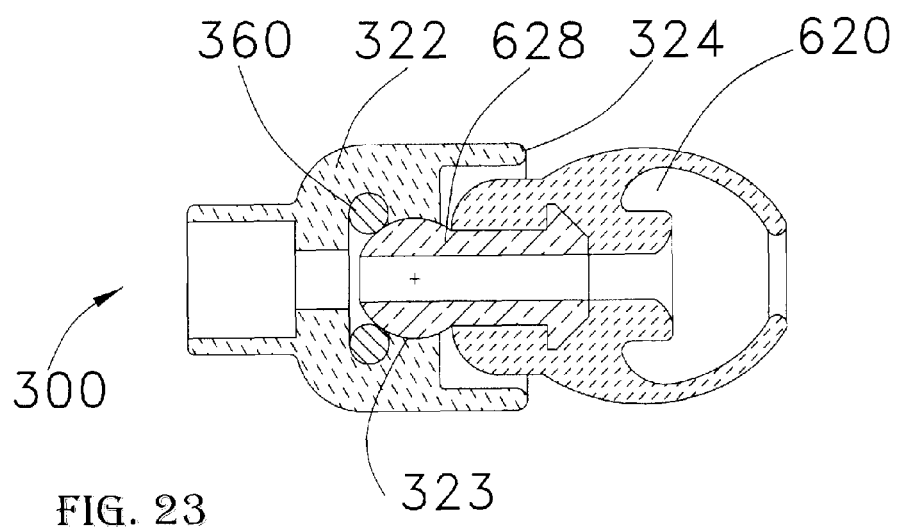

FIG. 23 is a cross section of the basic internal structure of a fourth embodiment of the present invention.

Figure 24:
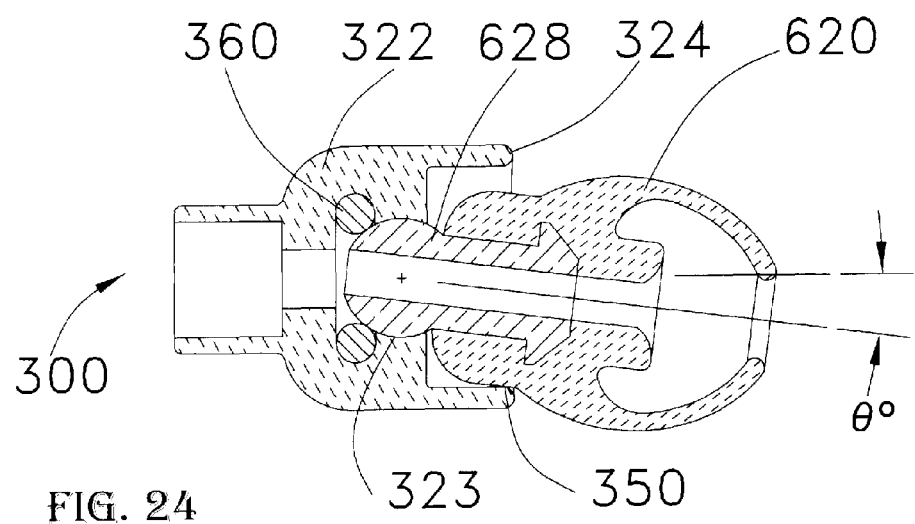

FIG. 24 is a cross section of the basic internal structure of the fourth embodiment of the invention with the ear tip portion swiveling in a downward direction.

Figure 25:
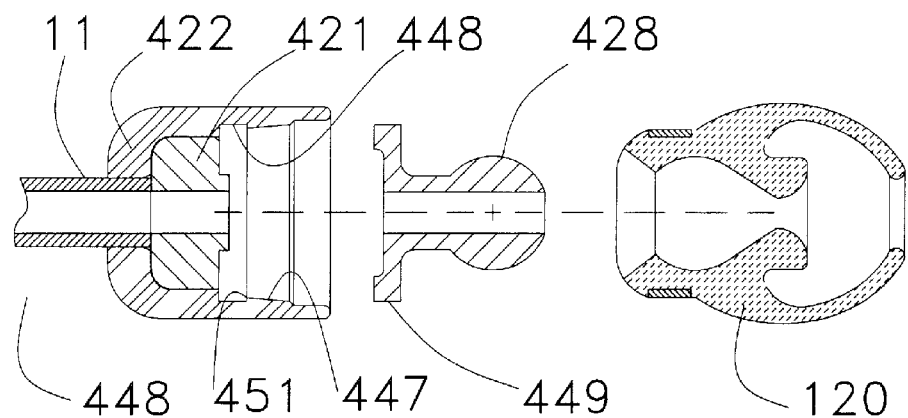

FIG. 25 is an exploded cross sectional view of the basic internal structure of a fifth embodiment of the present invention.

Figure 26:
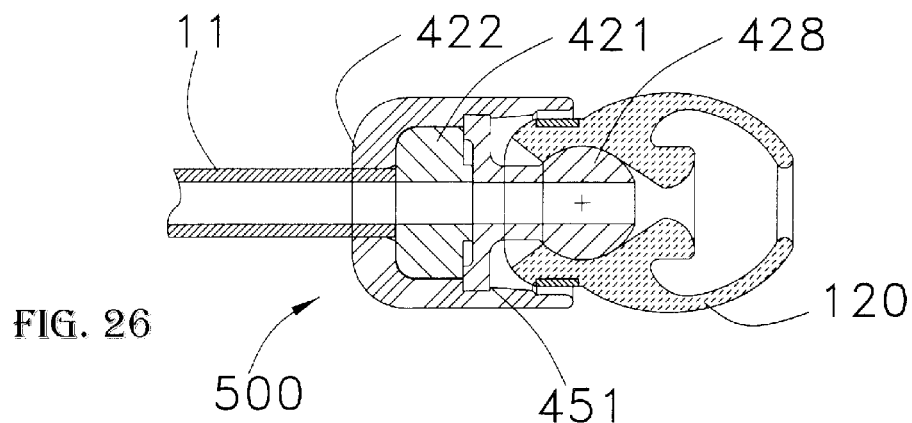

FIG. 26 is an assembled cross section of the basic internal structure of the fifth embodiment of the invention.

Figure 27:
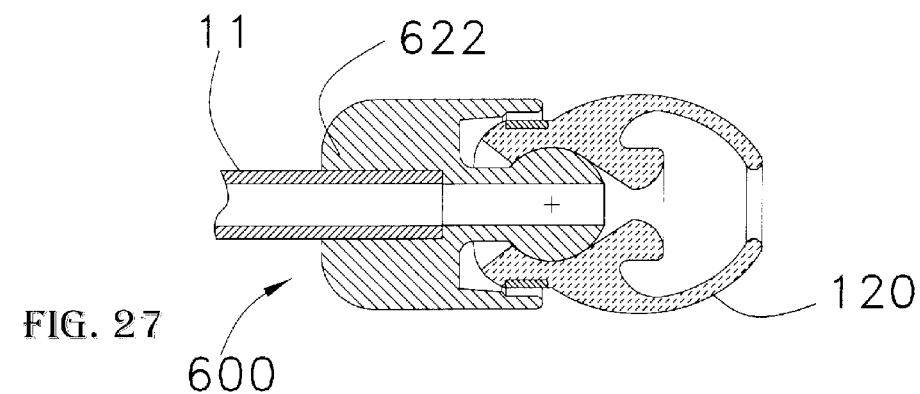

FIG. 27 is a cross section of the basic internal structure of a sixth embodiment of the present invention.

Figure 28:
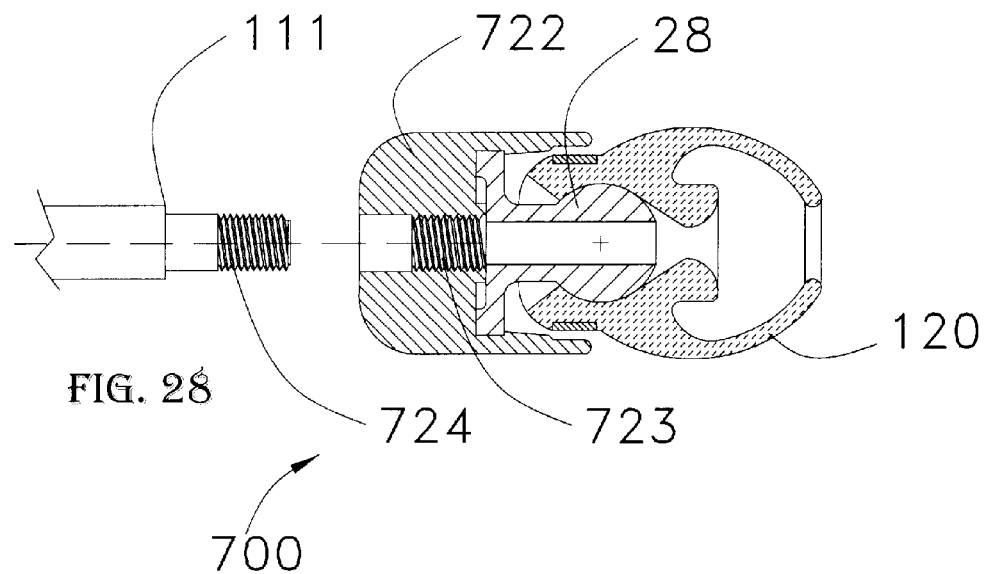

FIG. 28 is a cross section of the basic internal structure of a seventh embodiment of the present invention.

Figure 29:
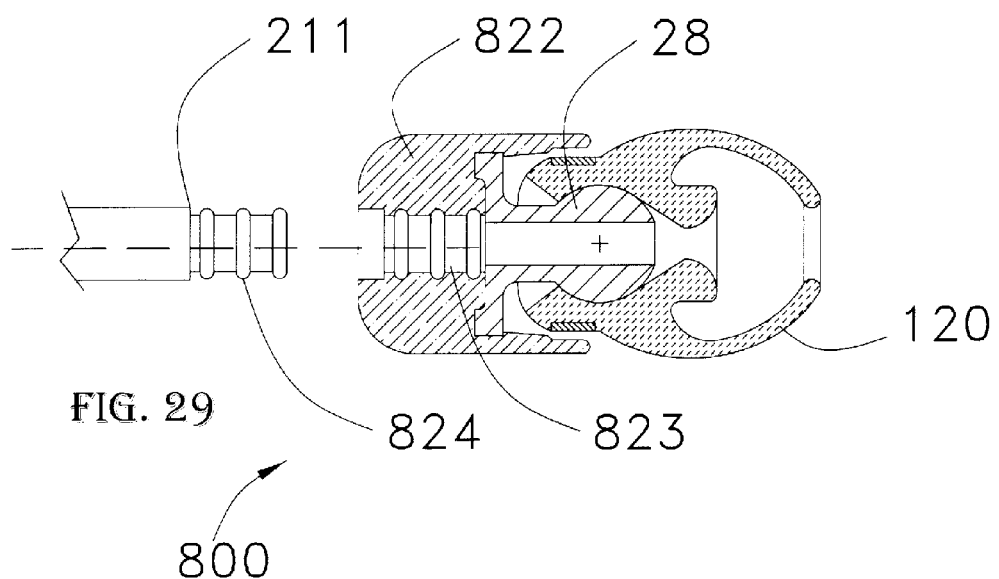

FIG. 29 is a cross section of the basic internal structure of an eighth embodiment of the present invention.

Figure 30:
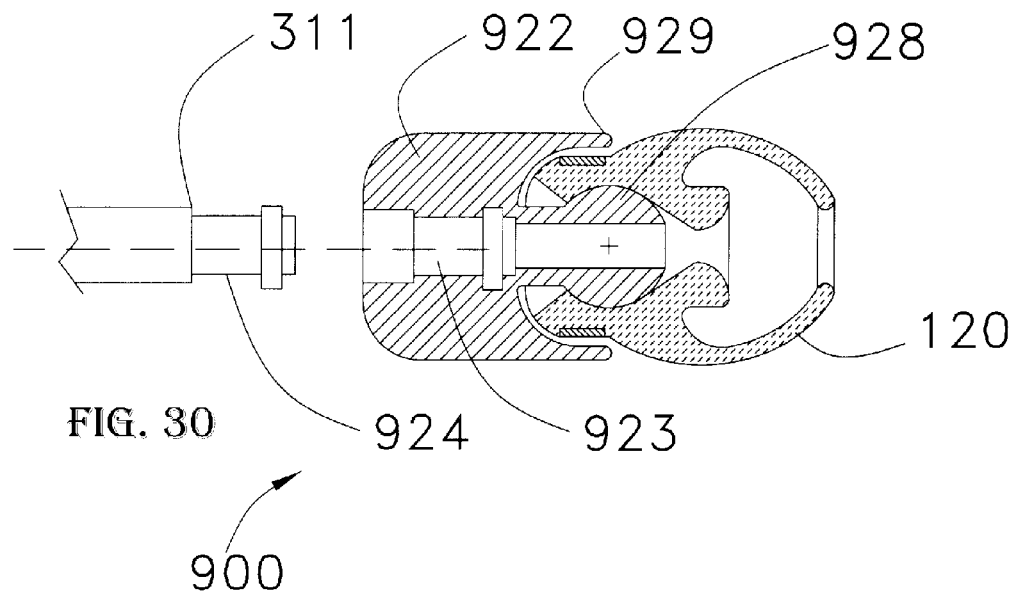

FIG. 30 is a cross section of the basic internal structure of a ninth embodiment of the present invention.

Figure 31:
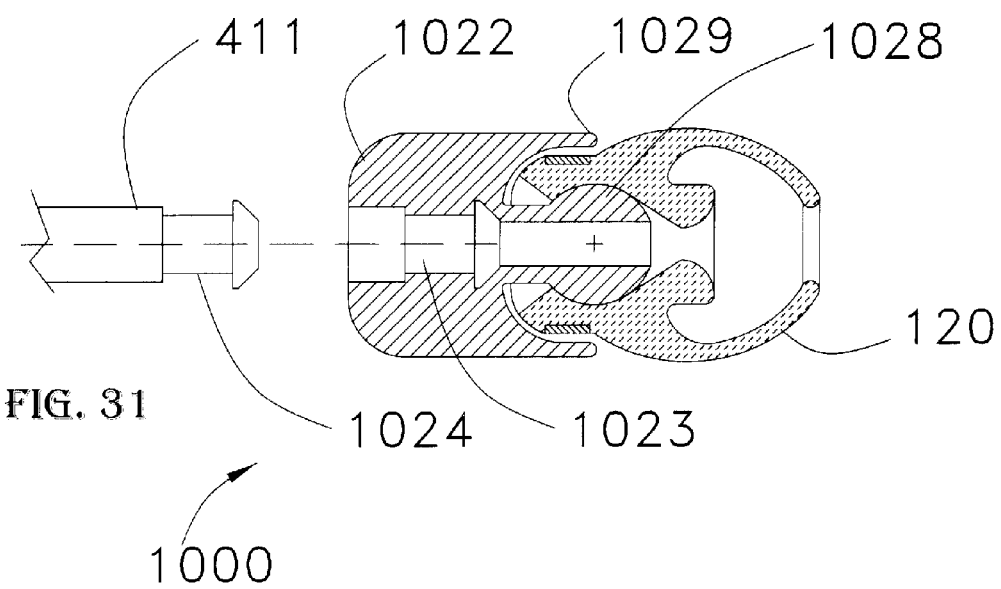

FIG. 31 is a cross section of the basic internal structure of a tenth embodiment of the present invention.

DETAILED DESCRIPTION OF THE PREFERRED EMBODIMENTS

Figure 1:
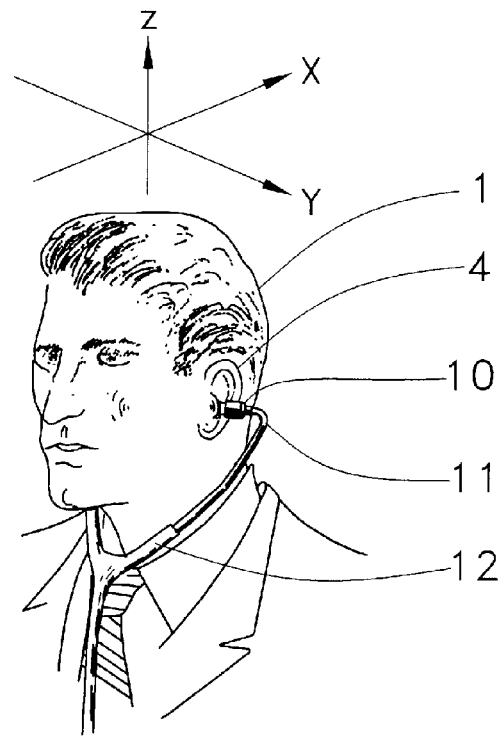
FIG. 1 shows a partial perspective view of a stethoscope with an embodiment of the inventive ear piece placed on each ear of a physician.
Figure 2:
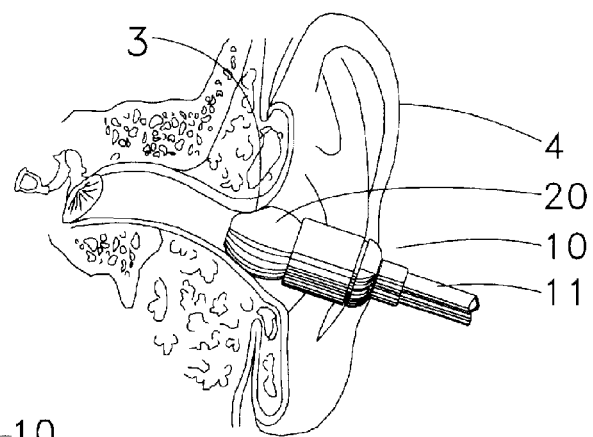
FIG. 2 shows a partial cut away view of a typical human ear with an embodiment of the inventive ear tip in place.

FIG. 1 is an illustration of a physician wearing a stethoscope of the present invention showing the position of the ear piece 10 attached to the metal tube portion 11, which connects to plastic lumen 12. FIG. 2 shows a close up cutaway view of the ear 4 and ear canal entrance 3 with ear piece 10 (of FIG. 1) in position. Note the distortion of ear piece 10's ear tip portion 20 at the entrance of the ear canal 3. This is normal for soft ear tips to affect proper sealing of the ear tip 20 to the ear canal entrance 3. Note also the angle of entry of the ear piece 10 relative to the horizontal plane. This entry angle (in the vertical plane of FIG. 2 which is parallel to the XZ plane of FIG. 3) can vary depending on the ear canal 3 entrance variations.

Figure 3:
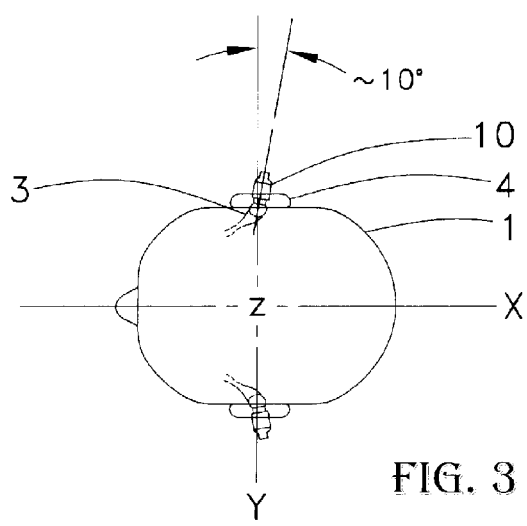
FIG. 3 shows diagrammatically a top view of a physician's head (with an embodiment of the inventive ear tip placed on each ear of the physician) indicating X, Y and Z coordinates referred to herein.

FIG. 3 is a diagram of the top view of the physician's head 1 showing ear pieces 10 (of FIGS. 1 and 2) in place. Axes X and Y (in a horizontal plane) are clearly shown in FIG. 3, whereas the vertical Z axis is perpendicular to the plane of FIG. 3. Note that the ear piece 10 is oriented (as is typical) about 10 degrees off the Y axis (in the XY plane) towards the back of the physician's ear 4 and thus his head 1. This angle (in the horizontal XY plane) is not the angle discussed with reference to FIG. 2 (FIG. 2 is in a plane parallel to the XZ plane of FIG. 3) but is another angle. Since the ear canal 3 is not perfectly round and the ear tip 20 is deformed in the canal 3, it is evident that the ear tip 20 needs to be free of movement and to sit in its position during use, while the body of the ear piece 10 with its tube 11 move both rotationally (typically 0-50 degrees from chest to top of head or so) about the earpiece axis and tangentially off axis some 5 to 10 degrees or so. This is limited freedom of motion is achieved in accordance with the present invention.

FIG. 7 illustrates an exemplary, typical stethoscope which includes an embodiment of the inventive ear pieces 10 (also shown in above-described FIGS. 1-3). The stethoscope comprises a head piece (comprising two ear pieces 10 mounted on sound tubes 11), a tube assembly (hollow flexible plastic lumens 12, transition 13, and lumen 14), and chest piece 15. Sound tubes 11 are over molded with lumens 12. The two lumens 12 join in a "y" transition 13 which then tapers to a single lumen 14. The single lumen 14 finally fastens to the chest piece 15 which is used for detecting body sounds by the physician. In some embodiments, the invention is a head piece (e.g., the stethoscope head piece of FIG. 7, or another stethoscope head piece, or audio headphones, or a telephone headset, or another non-stethoscope head piece) including at least one ear piece designed in accordance with an embodiment of the invention.

First Embodiment of the Present Invention

FIG. 8 shows a complete ear piece assembly 10 according to a first embodiment of the present invention. It comprises a soft ear tip 20, a main body 22 and a rear cover section 25. Rear cover section 25 is rigidly fastened to sound tube 11. Other parts of assembly 10 are not visible externally.

FIG. 9 is a half sectional view of assembly 10 of FIG. 8, showing the internal parts of the assembled ear piece 10. FIG. 10 shows the parts of FIG. 9 in an exploded view. Referring to FIG. 9 and FIG. 10, the structure of the ear piece 10 is shown. The entire assembly comprises the following:

sound tube 11, rear cover section 25 (through which sound transducer vent hole 32 extends, as shown in FIG. 10), sound transducer 24 (with wires 31 attached to transducer terminals 30), and gasket 23. Optionally, transducer 24 is omitted. Additionally, the assembly of FIGS. 9 and 10 includes ball joint unit 28 (with central through hole 26), ear tip 20, and main body 22. Optionally, a hole restrictor plug 29 is mounted in hole 26 to modify bass response of sound transducer 24. Hole restrictor plug 29 is generally not used if the speaker (sound transducer) 24 is omitted as in the case of a passive acoustic stethoscope. At least one hole 32 is formed through the rear cover section 25 if a speaker is used. This is for purposes of back sound pressure venting. This is standard practice in the art and will not be shown in any of the other drawings although it may be present.

During assembly, the sound tube 11 is inserted and bonded into rear cover section 25, while wires 31 are passed through rear cover section 25 and sound tube 11. Then, sound transducer 24 is fitted to the front portion of cover section 25. Now ball joint unit 28 and gasket 23 are fitted against the front side (the side facing right in FIG. 10) of cover section 25. Next, all these are then inserted into rear section of main body 22 as shown by the dotted line and arrow facing right in FIG. 10. Finally, ear tip 20 is inserted onto the protruding ball of ball joint unit 28. Preferably, spring clip 21 is positioned around ear tip 20 as shown, for increasing ear tip 20's capability to remain in a held position against unit 28's ball portion. As mentioned before the complete unit is shown in FIG. 9.

FIGS. 11 and 12 illustrate the off axis movement of the ear tip 20. The off axis pivoting movement of the ear tip 20 can be in the up direction, as shown in FIG. 12, or in the down direction, as shown in FIG. 11. Note that the proximal end portion (shroud section) of main body 22 defines a tubular cavity in which ear tip 20 can rotate ("on axis") or pivot ("off axis"), but that the shroud section limits ear tip 20's off axis movement at point 40 in FIG. 11 and at point 42 in FIG. 12. Note also that ear tip 20 has a large diameter portion, and that the shroud section of main body 22 is configured to limit off axis angular movement of ear tip 20 relative to body 22 by engaging ear tip 20's large diameter portion. The range of pivoting motion of ear tip 20 (relative to the ear piece assembly's longitudinal axis, labeled "X" in FIGS. 11 and 12) is limited to approximately ±10 degrees (the absolute magnitude of angle θ in FIGS. 11 and 12, and also in FIGS. 14, 22 and 24, is approximately 10 degrees). Allowing the ear tip 20 limited freedom to move (pivot) off axis and yet not too far so as to be cumbersome to insert into the ear canal (or to rub off, etc.) is a key feature of a class of embodiments of the present invention.

Second Embodiment of the Present Invention

FIG. 13 shows the internal structure of a second embodiment (ear piece 100) of the present invention. The entire assembly 100 comprises the following elements: sound tube 11, a rear cover section (corresponding to rear cover section 25 of FIG. 10), a sound transducer and gasket (corresponding to transducer 24 and gasket 23 of FIG. 10), ball joint unit 128 (with a central through hole), ear tip 320, and main body section 122. Ear piece 100 of FIG. 13 is similar to ear piece 10 of the first embodiment, but with its ball joint unit 128 having a hollow protrusion 129 (from its proximal end), said protrusion having a proximal opening 126. The ear tip 320 has also been provided with a larger opening 130 (larger than the corresponding opening of ear tip 20 of FIG. 10) to allow room for protrusion 129 to act as an off axis limiter for ear tip 320. The main body section 122 can now be shorter in length or remain the same (relative to main body section 22 of FIG. 10). In the FIG. 13 embodiment, the off axis motion limitation is provided by both the main body section 122 and the protrusion 129. The proximal end portion (shroud section) of main body section 122 defines a tubular cavity in which ear tip 320 can rotate ("on axis") or pivot ("off axis"), but the shroud section limits this off axis movement (e.g., at point 146 in FIG. 14). As shown in FIG. 14, protrusion 129 also limits the off axis movement of ear tip 320 (e.g., at point 46 in FIG. 14). The range of off axis pivoting motion of earpiece 320 (relative to the ear piece assembly's longitudinal axis, labeled "X" in FIG. 14) is limited to approximately ±10 degrees (the absolute magnitude of angle θ in FIG. 14 is approximately 10 degrees).

FIGS. 15, 16, and 17 show various configurations of the ear tip included in various embodiments of the invention.

FIG. 15 shows ear tip 20 (also shown in FIGS. 9 and 10) with outer (proximal) opening 50, inner opening 51, partially spherical ball joint socket opening 52 (whose proximal side tapers toward opening 51), and a distal opening 53 (defined by angled entry surface 54) for receiving a ball joint. Ear tip 20 will typically be made of a soft material such as silicone so as to deform when placed into the ear canal. Because it is soft it is prone to falling off if handled roughly. To assist retention on an earpiece ball joint, tip 20 has a slot for receiving a split spring metal collar or hard plastic ring 21 which may be round in cross section.

FIG. 16 shows an ear tip 120 with outer opening 60, inner opening 61, partially spherical ball joint socket opening 62 (whose proximal side tapers toward opening 61), and a distal opening 63 (defined by angled entry surface 64) for receiving a ball joint. This ear tip 120 will typically be made of a soft material such as silicone so as to deform when placed into the ear canal. Because it is soft it is prone to falling off if handled roughly. To assist retention on an earpiece ball joint, tip 120 has a slot for receiving a split spring plastic or metal collar 121 which is rectangular in cross section.

FIG. 17 shows an ear tip (220 and 221) with outer opening 70, inner opening 71, partially spherical ball joint socket opening 72 (whose proximal side tapers toward opening 71), and a distal opening 73 (defined by angled entry surface 74) for receiving a ball joint. Portion 220 of this ear tip will typically be made of a soft material such as silicone so as to deform when placed into the ear canal. The ear tip of FIG. 17 is a two part mold with a proximal portion 220 and a distal portion 221 (molded of a harder plastic material than is portion 220) to provide better holding on an earpiece ball joint.

FIGS. 18, 19, and 20 show various configurations of the ear tip distal openings 73, 83 and 93 of ear tips 420, 320, and 220/221, respectively.

Referring to FIG. 18, the preferred diameter of the partially spherical ball joint socket opening 82 of ear tip 420 should generally be of the same diameter as the ball of the ball joint unit 28. The smallest-diameter portion of opening 83 should generally be 0.7 times the diameter of the ball of unit 28 (illustrated as "x" dimension in FIG. 18). This creates a ball joint that is easy to push on and is adequate.

Referring to FIG. 19, the preferred diameter of the partially spherical ball joint socket opening 92 of ear tip 320 should generally be of the same diameter as the ball of the ball joint unit 328 (unit 328 differs from ball joint unit 28 by having a smaller diameter neck portion 330 and a smaller diameter central passage. The smallest-diameter portion of opening 93 can be 0.5 times the diameter of the ball of unit 328 (illustrated as "x" dimension in FIG. 19). This creates a ball joint that is harder to push on and has better retention. However, the neck portion 330 of ball joint unit 328 can be rather flimsy and prone to breaking unless it is made of metal. The preferred material for all the ball joint units is plastic. Metal is more expensive.

Referring to FIG. 20, the preferred diameter of the partially spherical ball joint socket opening 102 of ear tip 220, 221 should generally be of the same diameter as the ball of the ball joint unit 28. The smallest-diameter portion of opening 73 should generally be 0.7 times the diameter of the ball of unit 28. However as previously shown in FIG. 17 this ear tip unit 220, 221 is molded with a harder distal portion 221. In this case the dimension of the opening 73 is determined experimentally depending on the material used for distal portion 221. Also the lubricity of the plastics used determines the ease of rotation and swiveling of the ball and socket assembly. Teflon for the ball portion has shown the best results.

Third Embodiment of the Present Invention

FIGS. 21 and 22 show a cross sectional view of a third embodiment (ear piece assembly 200) of the present invention. Ear piece assembly 200 includes main body section 522 (whose proximal end portion 522A defines a generally cylindrical shroud), bearing element 529 within section 522, and ear tip 520 fitted onto element 529. Ear piece assembly 200 uses neither a relatively long sleeve nor a ball and socket joint. It does use element 529, which has a rather short hollow neck 530 and a hollow, partial conical (truncated conical), support portion 528 at its proximal end, in place of a ball joint unit.

Referring to FIG. 21, ear tip 520 of assembly 200 is designed to both rotate (rotate "on axis" about the assembly's longitudinal axis) and swivel (flex "off axis" relative to the assembly's longitudinal axis) relative to element 529. The sound seal is by a snug fitting of the ear tip's distal portion 524 to the neck 530 of element 529. The ear tip 520 is ribbed at portion 550 (between distal portion 524 and the rest of ear tip 520). The ribbed shape of portion 550 provides further ease of flexing off axis.

Referring to FIG. 22, ear tip 520 is shown in an off axis position. Off axis flexural pivoting movement of ear tip 520 (relative to element 529) is provided both by movement of ear tip 520's flexible distal portion 524 relative to element 529 and by flexing of ribbed portion 550. End portion 522A of ear tip housing 522 defines a tubular cavity in which ear tip 520 can rotate ("on axis") or pivot ("off axis"), but limits this off axis pivoting (e.g., as shown by shroud 522A's engagement with ear tip 520 at location 560). Cavity 523 within housing 522 is shown empty in FIGS. 21 and 22. It can house a sound transducer assembly for active stethoscopes or be fitted with an appropriate plastic bushing if a passive acoustic stethoscope is used.

In variations on the FIGS. 21-22 embodiment, element 529 is replaced by another bearing element having a rotationally symmetric support portion (e.g., a rotationally symmetric support portion having a shape other than the shape of partial conical end portion 528 of element 529), said bearing element being configured to support an ear tip that has been fitted onto it such that the ear tip has freedom to rotate ("on axis," where "axis" here denotes the axis of symmetry of the support portion) relative to the support portion. The ear tip should also have freedom to flex ("off axis") relative to the support portion (and relative to an ear tip housing in which the bearing element is positioned).

Fourth Embodiment of the Present Invention

FIGS. 23 and 24 show a cross sectional view of a fourth embodiment (ear piece assembly 300) of the present invention. Ear piece assembly 300 includes main body 322 (whose proximal end portion 324 defines a generally cylindrical shroud), element 628 rotatably mounted within body 322, and ear tip 620 attached (fastened or molded) onto element 628.

FIG. 23 shows a one piece molded housing 322 with a partial socket 323. Element 628 has a ball shaped proximal end, and is hollow (with an elongated shaft extending through it). When the ball shaped end portion of element 628 is pressed into the socket portion 323, it forms a rotating and swiveling ear piece assembly. If desired, an optional sealing "O" ring 360 provides a better acoustic seal between element 628 and main body 322. Although this sample embodiment is useful in an acoustic stethoscope, those in the art will appreciated that it could also be designed for provision of an acoustic transducer (e.g., for use in an active stethoscope).

FIG. 24 shows ear piece assembly 300 with ear piece 620 in an off axis position. Limitation of off axis pivoting of ear tip 620 is provided by shroud 324 of body 322 (as shown by shroud 324's engagement with ear tip 620 at location 350).

Fifth Embodiment of the Present Invention

FIGS. 25, 26 and 27 show a cross sectional view of a fifth embodiment (ear piece assembly 500) of the present invention. Ear piece assembly 500 includes main body (housing) 422 (whose distal end is attached to sound tube 11 and whose proximal end portion defines a generally cylindrical shroud), and ball joint unit 428 and ear tip 120 rotatably mounted within body 422 (with ear tip 120 attached to the ball end of unit 428).

FIG. 25 shows a cross sectional exploded view of ear piece assembly 500. In this exemplary embodiment, housing 422 is a one piece unit (once again having a capability of also housing a sound transducer). As shown, however, plastic bushing 421 is shown within housing 422 in a position for engaging distal flange 449 of unit 428, so as to allow on axis of rotation of unit 428 (with ear tip 120 fixedly attached thereto) relative to bushing 421 and housing 422. Ear tip housing 422 is provided with an inclined, inner very slight conical surface 447 for engaging the distal end portion of ear tip 120. This conical incline is preferably only about 2 to 3 degrees (relative to assembly 500's longitudinal axis). Immediately distal to surface 447 is a slightly larger diameter portion 448 of housing 422, designed to receive flange 449 of ball joint unit 428 (to snap unit 428 into housing 422). Portion 448 has an edge surface 451 at the intersection of portion 448 with surface 447.

FIG. 26 shows assembly 500 when it has been assembled. Note that sharply stepped edge surface 451 of housing 422 retains the ball joint unit 428. Ear tip 120 has been inserted over the ball end of unit 428 (with the ball end of unit 428 retained within a corresponding inner socket portion of ear tip 120 as shown in FIG. 26. Operation of assembly 500 is identical to that of other ear piece assemblies described and shown herein. Limitation of off axis pivoting of ear tip 120 is provided by the proximal shroud portion of housing 422 (the shroud engages ear tip 120 at the each limit of the off axis pivoting).

Sixth Embodiment of the Present Invention

FIG. 27 shows a cross sectional view of a sixth embodiment (ear piece assembly 600) of the invention. Assembly 600 includes a fully molded housing and ball unit 622. Unit 622 functions as both an ear tip housing and a ball section, with the ear tip housing and ball sections integrated together as one unit. Ear tip 120 is simply pushed on to the ball end of unit 622. This is the simplest unit designed for passive acoustic applications. Electronic, or active, stethoscopes can also use ear piece assemblies of this design if a sound transducer is placed elsewhere in the sound path, such as in the area 13 of FIG. 7 for example. This has been done many times in the art. With appropriate plastic injection molding techniques, this one piece unit could be designed to hold a sound transducer also (e.g., if sound tube 11, for example, is modified for a larger diameter at its proximal end). In this case, unit 622 could have a distal portion with a hole large enough to hold a sound transducer and the modified tube 11. Operation of assembly 600 is identical to that of other ear piece assemblies described and shown herein. Limitation of off axis pivoting of ear tip 120 is provided by the proximal shroud portion of unit 622 (the shroud engages ear tip 120 at the each limit of the off axis pivoting).

Seventh Embodiment of the Present Invention

FIG. 28 shows a cross sectional view of a seventh embodiment (ear piece assembly 700) of the invention. Assembly 700 can be employed for retro-fitting a common type of commercial stethoscope. Referring to FIG. 28, assembly 700 includes ear tip housing 722 fitted with a threaded distal portion 723 configured to receive threaded proximal portion 724 of sound tube 111 (so that housing 722 can be screwed onto the proximal end of tube 111). Fitted into the proximal end of housing 722 is ball joint unit 28 which receives ear tip 120. Limitation of off axis pivoting of ear tip 120 is provided by the proximal shroud portion of housing 722 (the shroud engages ear tip 120 at the each limit of the off axis pivoting).

Eighth Embodiment of the Present Invention

FIG. 29 shows a cross sectional view of an eighth embodiment (ear piece assembly 800) of the invention. Assembly 800 can be employed for retro-fitting a second common type of commercial stethoscope. Referring to FIG. 29, assembly 800 includes ear tip housing 822 fitted with a second style portion 823 configured to receive second style proximal portion 824 of sound tube 211 (so that housing 822 can be attached onto the proximal end of tube 211). Fitted into proximal end of housing 822 is ball joint unit 28 which receives ear tip 120. Limitation of off axis pivoting of ear tip 120 is provided by the proximal shroud portion of housing 822 (the shroud engages ear tip 120 at the each limit of the off axis pivoting).

Ninth Embodiment of the Present Invention

FIG. 30 shows a cross sectional view of a ninth embodiment (ear piece assembly 900) of the invention. Assembly 900 can be employed for retro-fitting a third common type of commercial stethoscope. Referring to FIG. 30, assembly 900 includes ear tip housing 922 fitted with a third style portion 923 configured to receive third style proximal portion 924 of sound tube 311 (so that housing 922 can be attached onto the proximal end of tube 311). Proximal ball joint portion unit 928 of housing 922 receives ear tip 120. Limitation of off axis pivoting of ear tip 120 is provided by the proximal shroud portion 929 of housing 922 (shroud 929 engages ear tip 120 at the each limit of the off axis pivoting).

Tenth Embodiment of the Present Invention

FIG. 31 shows a cross sectional view of a tenth embodiment (ear piece assembly 1000) of the invention. Assembly 1000 can be employed for retro-fitting a fourth common type of commercial stethoscope. Referring to FIG. 31, assembly 1000 includes ear tip housing 1022 fitted with a fourth style portion 1023 configured to receive fourth style proximal portion 1024 of sound tube 411 (so that housing 1022 can be attached onto the proximal end of tube 411). Proximal ball joint portion unit 1028 of housing 1022 receives ear tip 120. Limitation of off axis pivoting of ear tip 120 is provided by the proximal shroud portion 1029 of housing 1022 (shroud 1029 engages ear tip 120 at the each limit of the off axis pivoting).

The materials available for the present invention are many. For example typical embodiments of the ear piece housing can be metal (e.g., aluminum) or plastic (e.g., polycarbonate or nylon). Typical embodiments of the ear tip can be silicone or polyurethane or another soft material. Typical embodiments of the ball joint can be made of any suitable plastic or metal. Teflon has been used successfully for the ball joint.

Typical embodiments the rotating and swivel unit (e.g., element 529 of FIGS. 21 and 22) are preferably made of plastic for cost reasons, but could alternatively be made of metal.

In embodiments in which the ear piece housing has a main housing section, the main housing section can be made as one uniform piece, or as several pieces coupled together, and can be made of any of various materials (e.g., plastic, metal, or a composite material.

Some embodiments of the invention are or include a ball joint unit, said ball joint unit including: a flange shaped distal section with a hole through axial center for sound propagation; a short cylindrical shaft center section with a hole through axial center for sound propagation; and a ball proximal section with a hole through axial center for sound propagation, where the holes from the distal end of said flange section through to the proximal end of said ball section are generally one through hole.

Some embodiments of the invention are or include a ball joint unit, said ball joint unit including: a flange shaped distal section with a hole through axial center for sound propagation; a short cylindrical shaft center section with a hole through axial center for sound propagation; a ball central section with a hole through axial center for sound propagation; and a tubular section affixed to said proximal end of ball central section with a hole through axial center for sound propagation, wherein the holes from the distal end of said flange section through to the proximal end of said tubular section are generally one through hole.

Some embodiments of the invention are or include a conical (e.g., blunt or truncated conical) ended shaft unit, said conical ended shaft unit including: a flange shaped distal section with a hole through axial center for sound propagation; a short cylindrical shaft center section with a hole through axial center for sound propagation; and a blunt conical proximal section with the lesser diameter of said conical section facing the proximal direction with a hole through axial center for sound propagation, wherein the larger diameter conical section faces in the distal direction, the larger diameter conical section is substantially larger in diameter than the shaft section, the smaller diameter conical section is approximately the same diameter as the shaft section, and the holes from the distal end of said flange section through to the proximal end of said conical section are generally one through hole.

The present invention is universally applicable to most existing stethoscopes and dictation headsets on the market, and is also useful to implement ear piece assemblies of other headsets.

In terms of limiting the off axis movement of the ear tip (of the inventive assembly) and its tendencies to be rubbed off during use or stuffing into a pocket on a surgical gown, for example, the present inventor has not limited his scope of possible design variations. Rather he has presented in this teaching some of the most practical designs. Key to the teaching of this disclosure is ear tip's freedom to undergo limited "off axis" movement (and preferably also, free "on axis" rotation). Those of ordinary skill in the art could readily devise other means to limit "off axis" movement and provide ear tip retention, given the teaching of this disclosure.

Although the descriptions above contain many specificities, these should not be construed as limiting the scope of the invention but as merely providing illustrations of some of the presently preferred embodiments of this invention. Thus the scope of the invention should be determined by the appended claims and their legal equivalents rather than by the examples provided.

What is claimed is:

1. A stethoscope, including:
a chest piece;
a head piece; and
a stethoscope tube assembly coupled between the chest piece and the head piece, wherein the
head piece includes at least one ear piece assembly including:
an ear tip;
a bearing mounted to the ear tip; a housing body having a longitudinal axis and a proximal end portion, wherein the proximal end portion defines a tubular cavity, a distal portion of the ear tip and at least a portion of the bearing are positioned within the tubular cavity such that the ear tip has freedom to rotate about the longitudinal axis relative to the housing body and to undergo limited off axis angular movement relative to said housing body, and the proximal end portion of the housing body is configured to limit off axis angular movement of the ear tip relative to said housing body but to allow the limited off axis angular movement of the ear tip relative to said housing body.

2. The stethoscope of claim 1, also including:
an acoustic transducer within the housing body.

3. The stethoscope of claim 1, wherein the housing body defines at least one sound venting hole.

4. The stethoscope of claim 1, wherein the bearing is a ball joint unit, and the ear tip has freedom to rotate about the longitudinal axis relative to the ball joint unit and limited freedom to undergo off axis angular movement relative to said ball joint unit.

5. The stethoscope of claim 1, wherein bearing is a ball joint unit, the ball joint unit has a proximally extending protrusion, and each of the protrusion and the proximal end portion of the housing body is configured to limit off axis angular movement of the ear tip relative to said housing body while allowing limited off axis angular movement of the ear tip relative to said housing body.

6. The stethoscope of claim 5, wherein the proximally extending protrusion is an integral tubular section of the ball joint unit.

7. The stethoscope of claim 1, wherein the bearing is a ball joint unit and the housing body defines a partial spherical opening designed to accept at least a part of the ball joint unit.

8. The stethoscope of claim 1, wherein the ear tip has a large diameter portion, and the proximal end portion of the housing body is configured to limit off axis angular movement of the ear tip relative to said housing body by engaging the large diameter portion of the ear tip.

9. The stethoscope of claim 1, wherein the bearing is a bearing element having a rotationally symmetric support portion, said bearing element is configured to support the ear tip such that the ear tip has freedom to rotate about the longitudinal axis relative to the support portion and the housing body, the ear tip configured to undergo angular flexural movement relative to the support portion and the housing body, and the proximal end portion of the housing body is configured to limit off axis angular flexural movement of the ear tip relative to said housing body but to allow limited off axis angular flexural movement of the ear tip relative to said housing body.

10. The stethoscope of claim 9, wherein the support portion of the bearing element is a partial conical end portion of said bearing element.

11. The stethoscope of claim 1, wherein the ear tip is configured to have limited freedom to undergo angular flexural movement relative to the housing body, and the proximal end portion of the housing body is configured to limit off axis angular flexural movement of the ear tip relative to said housing body but to allow limited off axis angular flexural movement of the ear tip relative to said housing body.

12. The stethoscope of claim 1, wherein the bearing and the housing body are portions of a single, integrated housing and ball unit.

13. A head piece including at least one ear piece assembly, each said ear piece
assembly including:
an ear tip;
a bearing mounted to the ear tip;
a housing body having a longitudinal axis and a proximal end portion, wherein the proximal end portion defines a tubular cavity, a distal portion of the ear tip and at least a portion of the bearing are positioned within the tubular cavity such that the ear tip has freedom to rotate about the longitudinal axis relative to the housing body and to undergo limited off axis angular movement relative to said housing body, and the proximal end portion of the housing body is configured to limit off axis angular movement of the ear tip relative to said housing body but to allow the limited off axis angular movement of the ear tip relative to said housing body.

14. The head piece of claim 13, also including:
an acoustic transducer within the housing body.

15. The head piece of claim 13, wherein the housing body defines at least one sound venting hole.

16. The head piece of claim 13, wherein the bearing is a ball joint unit, and the ear tip has freedom to rotate about the longitudinal axis relative to the ball joint unit and limited freedom to undergo off axis angular movement relative to said ball joint unit.

17. The head piece of claim 13, wherein bearing is a ball joint unit, the ball joint unit has a proximally extending protrusion, and each of the protrusion and the proximal end portion of the housing body is configured to limit off axis angular movement of the ear tip relative to said housing body while allowing limited off axis angular movement of the ear tip relative to said housing body.

18. The head piece of claim 17, wherein the proximally extending protrusion is an integral tubular section of the ball joint unit.

19. The head piece of claim 13, wherein the bearing is a ball joint unit and the housing body defines a partial spherical opening designed to accept at least a part of the ball joint unit.

20. The head piece of claim 13, wherein the ear tip has a large diameter portion, and the proximal end portion of the housing body is configured to limit off axis angular movement of the ear tip relative to said housing body by engaging the large diameter portion of the ear tip.

21. The head piece of claim 13, wherein the bearing is a bearing element having a rotationally symmetric support portion, said bearing element is configured to support the ear tip such that the ear tip has freedom to rotate about the longitudinal axis relative to the support portion and the housing body, the ear tip configured to undergo angular flexural movement relative to the support portion and the housing body, and the proximal end portion of the housing body is configured to limit off axis angular flexural movement of the ear tip relative to said housing body but to allow limited off axis angular flexural movement of the ear tip relative to said housing body.

22. The head piece of claim 21, wherein the support portion of the bearing element is a partial conical end portion of said bearing element.

23. The head piece of claim 13, wherein the ear tip is configured to have limited freedom to undergo angular flexural movement relative to the housing body, and the proximal end portion of the housing body is configured to limit off axis angular flexural movement of the ear tip relative to said housing body but to allow limited off axis angular flexural movement of the ear tip relative to said housing body.

24. The head piece of claim 13, wherein the bearing and the housing body are portions of a single, integrated housing and ball unit.

25. An ear piece assembly, including: a bearing, configured to be mounted to an ear tip so as to support the ear tip; and a housing body having a longitudinal axis and a proximal end portion, wherein the proximal end portion defines a tubular cavity configured to receive a distal portion of the ear tip and at least a portion of the bearing such that such that the ear tip has freedom to rotate about the longitudinal axis and to undergo limited off axis angular movement relative to said housing body, and the proximal end portion of the housing body is configured to limit off axis angular movement of the ear tip relative to said housing body but to allow the limited off axis angular movement of the ear tip relative to said housing body.

26. The assembly of claim 25, wherein the housing body includes:
a main housing section whose proximal end portion defines the tubular cavity; and
a back cap section, having a distal end portion configured to accept a head piece sound tube, and a proximal end portion attached to the main housing section.

27. The assembly of claim 26, wherein the main housing section includes a slight conical cavity section with a larger diameter portion of said conical cavity facing a proximal end of the main housing, the bearing is a ball joint unit having a ball section on a proximal end and a flange section on a distal end and a short shaft section between the ball section and the flange section, and the main housing section includes a ring cavity section molded at a distal end of the slight conical cavity section and configured to snap in and capture said flange portion of said ball joint unit.

28. The assembly of claim 25, also including:
an acoustic transducer within the housing body.

29. The assembly of claim 25, wherein the housing body defines at least one sound venting hole.

30. The assembly of claim 25, said assembly also including an ear tip attached to the bearing, wherein said bearing is a ball joint unit, and the ear tip has freedom to rotate about the longitudinal axis relative to the ball joint unit and limited freedom to undergo off axis angular movement relative to said ball joint unit.

31. The assembly of claim 25, said assembly also including an ear tip attached to the bearing, wherein said bearing is a ball joint unit, the ball joint unit has a proximally extending protrusion, and each of the protrusion and the proximal end portion of the housing body is configured to limit off axis angular movement of the ear tip relative to said housing body while allowing limited off axis angular movement of the ear tip relative to said housing body.

32. The assembly of claim 31, wherein the proximally extending protrusion is an integral tubular section of the ball joint unit.

33. The assembly of claim 25, said assembly also including an ear tip attached to the bearing, wherein the ear tip has a large diameter portion, and the proximal end portion of the housing body is configured to limit off axis angular movement of the ear tip relative to said housing body by engaging the large diameter portion of the ear tip.

34. The assembly of claim 25, said assembly also including an ear tip attached to the bearing, and wherein the bearing is a bearing element having a rotationally symmetric support portion, said bearing element is configured to support the ear tip such that the ear tip has freedom to rotate about the longitudinal axis relative to the support portion and the housing body, the ear tip configured to undergo angular flexural movement relative to the support portion and the housing body, and the proximal end portion of the housing body is configured to limit off axis angular flexural movement of the ear tip relative to said housing body but to allow limited off axis angular flexural movement of the ear tip relative to said housing body.

35. The assembly of claim 34, wherein the support portion of the bearing element is a partial conical end portion of said bearing element.

36. The assembly of claim 25, said assembly also including an ear tip attached to the bearing, wherein the ear tip is configured to have limited freedom to undergo angular flexural movement relative to the housing body, and the proximal end portion of the housing body is configured to limit off axis angular flexural movement of the ear tip relative to said housing body but to allow limited off axis angular flexural movement of the ear tip relative to said housing body.

37. The assembly of claim 25, wherein the bearing is a ball joint unit and the housing body defines a partial spherical opening designed to accept at least a part of the ball joint unit.

38. The assembly of claim 25, wherein the bearing and the housing body are portions of a single, integrated housing and ball unit.

39. An ear tip, including:
a body made of soft, deformable material, and having a distal opening configured to receive a ball joint, said ball joint having a hole for sound propagation, wherein the body also has:
a thin walled, generally partially egg shaped ear tip proximal end configured to deform into sealing engagement with a user's ear canal, said proximal end defining a proximal outer opening;
a partial spherical inner surface configured to grip the ball joint after said ball joint has been inserted through the distal opening into engagement with said partial spherical inner surface; and
an inner proximal opening, between the partial spherical inner surface and the proximal end, whose function is sound propagation.

40. The ear tip of claim 39, including:
a split metal reinforcing ring on an outer distal portion of said body, said ring being configured to increase engagement force exerted by the body on a ball joint gripped within the partial spherical inner surface.

41. The ear tip of claim 39, including:
a plastic reinforcing ring on an outer distal portion of said body, said ring being configured to increase engagement force exerted by the body on a ball joint gripped within the partial spherical inner surface.

42. The ear tip of claim 39, including:
an elastomeric reinforcing ring on an outer distal portion of said body, said ring being configured to increase engagement force exerted by the body on a ball joint gripped within the partial spherical inner surface.

43. An ear tip, including:
a body made of soft, deformable material, and having a distal opening configured to receive a ball joint, said ball joint having a hole for sound propagation, wherein the body also has:
a generally cylindrical opening of such dimension so as to leave a relatively thin wall on a distal approximate half of the body, wherein the distal opening is of substantially lesser diameter than is said cylindrical opening;
an inner proximal opening whose function is sound propagation; and
a thin walled, generally partially egg shaped proximal end configured to deform into sealing engagement with a user's ear canal, and defining an outer proximal opening.

* * * * *